United States Patent [19]
Shanel

[11] Patent Number: 4,583,946
[45] Date of Patent: * Apr. 22, 1986

[54] HOLDER FOR RUBBER DENTAL DAM

[76] Inventor: Kathleen A. Shanel, St. Charles, Ill. 60174

[*] Notice: The portion of the term of this patent subsequent to Apr. 23, 2002 has been disclaimed.

[21] Appl. No.: 167,837

[22] Filed: Jul. 14, 1980

Related U.S. Application Data

[63] Continuation-in-part of Ser. No. 790,567, Apr. 25, 1977, Pat. No. 4,215,477, and a continuation-in-part of Ser. No. 85,252, Oct. 16, 1979, Pat. No. 4,512,742.

[51] Int. Cl.$^4$ .............................................. A61C 5/12
[52] U.S. Cl. .................................................... 433/136
[58] Field of Search ......................... 433/136, 137, 138

[56] References Cited

U.S. PATENT DOCUMENTS

| | | | |
|---|---|---|---|
| 296,992 | 4/1884 | Moffitt | 433/137 |
| 682,308 | 9/1901 | Young | 433/137 |
| 702,394 | 6/1902 | Beall | 433/137 |
| 1,207,756 | 12/1916 | Holmes | 433/137 |
| 3,406,452 | 10/1968 | McConville | 433/137 |
| 4,204,329 | 5/1980 | Kahn | 433/136 |
| 4,215,477 | 8/1980 | Shanel | 433/136 |

OTHER PUBLICATIONS

"Orthodontics Principles and Practice" by T. M. Graber, pp. 77,78,207,228,248,249.
"McConville Dam" ad, 10/79, pp. 9,10.
"Ostby Rubber Dam Frame" Ad, Hygienic Pamphlet, 1962.

*Primary Examiner*—John J. Wilson
*Attorney, Agent, or Firm*—Laff, Whitesel, Conte & Saret

[57] ABSTRACT

A facial frame having an arcuate bottom bar which rests on and pivots about the pogonion on the front of the chin with an arcuate portion which surrounds a greater arcuate portion of the patient's face than has been used heretofore. The bottom bar terminating on opposite ends in upright positions which pass on either side of the patient's head and face as the bottom bar pivots about said pogonion. The frame includes fasteners for securing a dental dam, preferably made from a thin rubber sheet. The frame has fasteners which are oriented so that the dam may be attached to them after it has been installed over the patient's teeth. Other fasteners are on the frame and positioned so that dental tape may be used to tie it in place about a patient's head. The geometry is such that the dental dam does not restrict either the working or the visible area of the patient's mouth, and further such that the frame forms a stable support for the dentist or hand tools.

9 Claims, 13 Drawing Figures

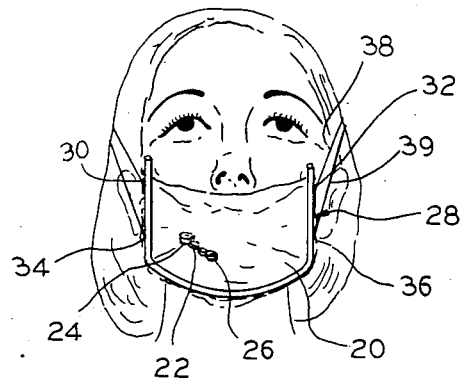
FIG. 1
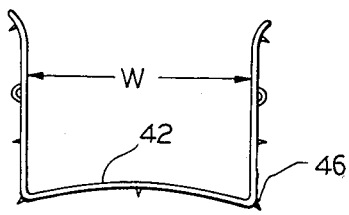
FIG. 2
(PRIOR ART)
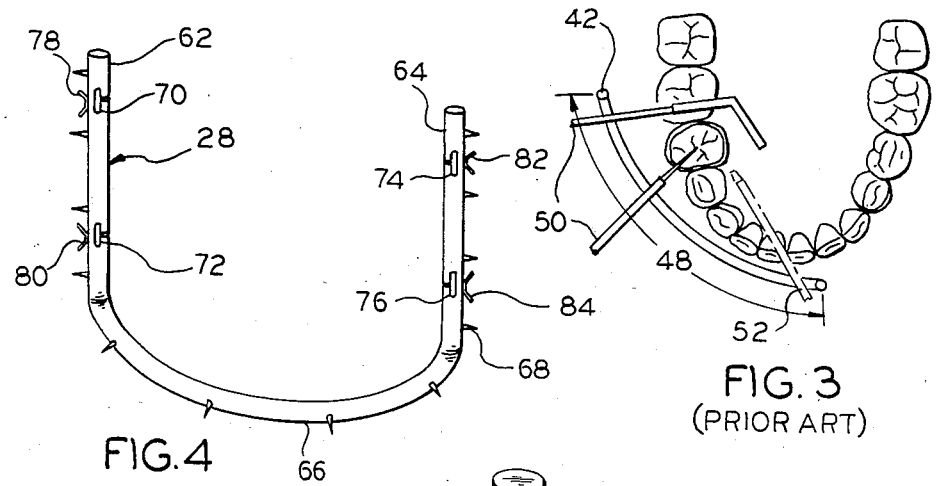
FIG. 3
(PRIOR ART)
FIG. 4
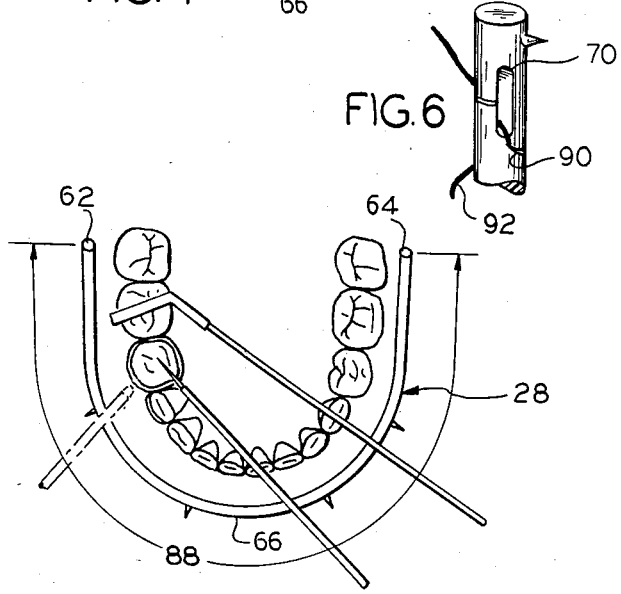
FIG. 6
FIG. 5
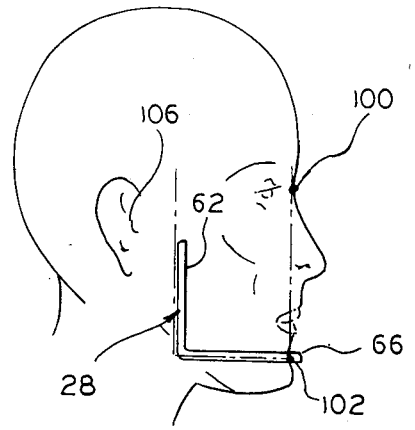
FIG. 7

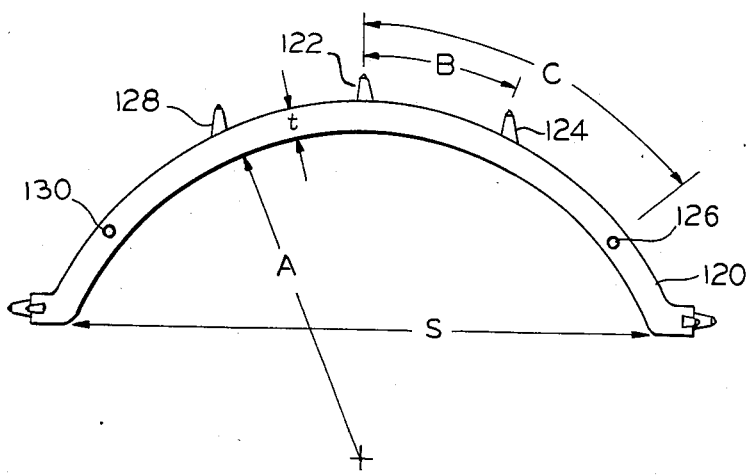
FIG. 8
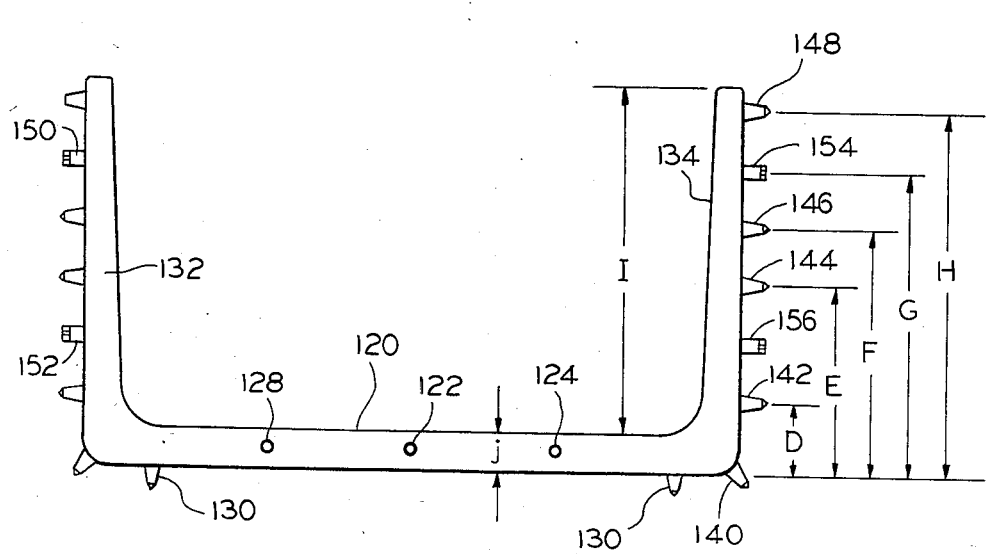
FIG. 9
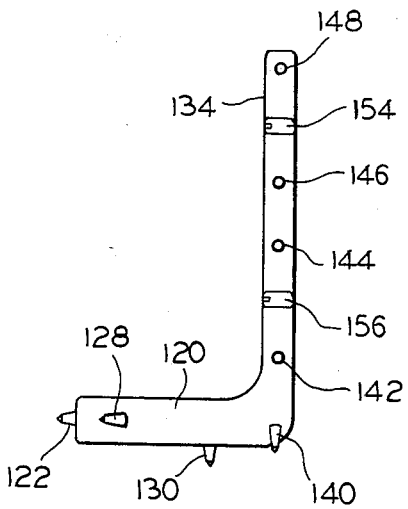
FIG. 10
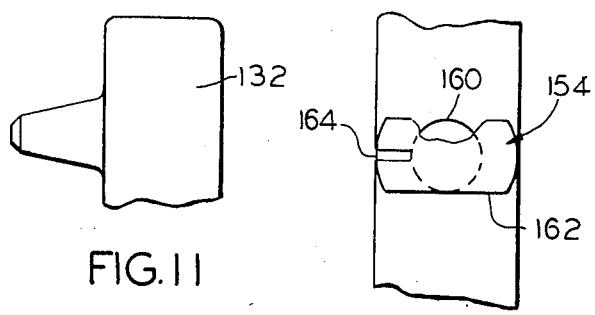
FIG. 11
FIG. 12
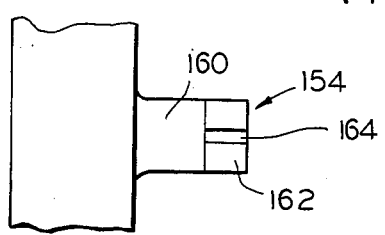
FIG. 13

HOLDER FOR RUBBER DENTAL DAM

This is a continuation-in-part of my earlier applications Ser. No. 790,567, filed Apr. 25, 1977, now U.S. Pat. No. 4,215,477, 8/5/80, and Ser. No. 085,252, filed Oct. 16, 1979, now U.S. Pat. No. 4,512,742, 04/28/85.

This invention relates to dental appliances and, more particularly, to frame holders for dental dams.

The rubber dam was introduced into dentistry about 1864, in order to ensure complete dryness and cleanliness of the teeth. More particularly, a rubber dam is used to isolate a tooth or the individual teeth being treated. It eliminates saliva from the location of treatment and guards against contamination, because the cavity preparation is initiated and completed without contact by or contamination from the fluids of the mouth. It also protects the patient from the possibility of aspirating or swallowing debris associated with preparation and restoration of the tooth. It retracts the lips, cheeks, tongue, and the marginal tissue to a mild degree, thereby providing better access and vision and protecting the soft tissues from medications that may be irritating or distasteful. However, the retraction is often painful, leaving red marks on the patient's face where the dam has stressed the skin. Regardless of which method is used, the resulting structure usually presses uncomfortably against the patient's facial tissues, leaving the red stress marks noted above. The upper lip and corners of the patient's mouth must be lubricated to prevent chafing. The patient's eyes might be injured unless extreme care is taken to prevent the frame from striking the eye, especially if one end of an elastic head strap should come loose and snap the frame toward the eye. This is especially true if either the dam or harness is stretched so that it could snap, if it breaks loose.

The dam is usually stretched over and hooked onto a frame, which is tied around the head of the patient. A difficulty with the prior art frames is that they have tended to restrict the arcuate field over which the dentist and dental assistants may work. Moreover, whether used with or without the prior art frames, the cloth or "Velcro" straps behind the head are transferred from patient to patient, thereby carrying germs, oils, and the like, from patient to patient. The straps have been difficult to attach, often requiring the aid of an assistant. Also, the straps may tend to disarray the patient's coiffure.

One frame for holding dental dams is seen in U.S. Pat. No. 3,406,452, granted to Richard S. McConville, on Oct. 22, 1969. McConville states that the rising vertical bars of his frame must fit the face in the area of the cheekbones. Therefore, the upper ends of his vertical frame bars flare outwardly (at angles which he identifies as angles A and B), in order to more nearly fit the contours of the face, over the cheekbones. One result of this facial fit over the cheekbones is that McConville had to place ¼-inch balls on the ends of the uprights in order to protect the patient's eyes.

The McConville frame is dependent on a single elastic strap for support and retraction. If it was snapped or unhooked accidentally, the frame can be violently pulled to one side, thus endangering the eye, regardless of the ¼" steel balls. Without the strap, the frame can be easily rotated causing the left or right frame arm to go up or down. McConville also states that the base of the frame must not press against the patient's chin. Therefore, in order to provide the retraction of the cheeks possible with the Shanel frame, it is necessary for the McConville frame to go below the chin causing the rubber sheet to wrap over the lower lip and around the chin, thereby applying painful pressure.

I have found that a dental dam frame is much more comfortable to the patient and produces far fewer stress marks on their faces if a totally different fit is used as compared to the fit used by McConville. The Shanel frame is designed to incorporate an important base curvature and shorter vertical arm creating more stability and safer application. The fit is such that the vertical arms are placed beyond the cheek bones. The bottom of my frame rests in the notch between the lower lip and the bottom of the chin; therefore, it does not cause the rubber sheet to wrap around the chin. At this location, the frame, not the patient's face, takes the stress of the stretched rubber. The difference is plainly seen by almost anyone who looks at the stress marks or absence of stress marks on a patient's face after the two dental dam frames have been used.

Instead of restricting the movement of the frame uprights by resting them on the cheek bones, I make the base portion of the frame wide enough to keep the uprights away from and on opposite sides of the face and head. This way, the frame uprights and pivots around a point of contact on the chin. The uprights swing about this pivot point until they come to rest at a point of minimum rubber sheet tension, with the uprights in a generally vertical orientation (relative to the normal head position) which is substantially parallel to the facial plane. It is irrelevant whether the patient's facial plane slants back or forward since the uprights tend to become parallel to the individual's facial plane regardless of what it is.

The unique use of two straps, preferably made of disposable dental tape, allows for increased stability due to the nonelastic, plural nature of the straps. On testing in the field, it has been determined that the greater curvature creates a stable system with or without the straps due to the rubber sheet's tension distribution on the frame. The effect is force, originating from the teeth, spreading on the frame which curves around the face. McConville's frame relies on the elastic strap to pull the frame posterior toward the face to gain retraction and stability.

Another important difference between the McConville frame and my frame is that his frame is made of metal while mine is made of a plastic, such as white nylon. This use of plastic is important for two reasons. First, by far the greatest use of this type of dental dam frame is during procedures (such as root canals) which require X-ray images. Thus, it is usually necessary to remove metal frames—but not plastic frames—in order to complete the X-ray pictures. Second, dental dam frames are often placed in sterilizing equipment and repeatedly heated. Metal could eventually be damaged by repeated heating and cooling cycles. However, the plastic which I use is cured a little more, each time that it is heated to sterilization temperatures. Therefore, my plastic frame actually becomes stronger, the longer that it is used.

McConville stresses that he only has to provide two sizes of frames, one for adults and another for children. This is because the size of human heads is remarkably uniform and does not vary significantly for normal people. Growth is substantially the only cause for variations in head size. During much of the period of maximum growth (e.g., from birth to, perhaps, six years old), a child does not have many teeth. In fact, during the first two years of life, the child has no teeth. Most children do not see a dentist until they are about to enter school at the age of five or six years, which is after the period of maximum growth-related changes in head size. Accordingly, as McConville points out, the fit of the frame does not depend upon differences in the size of human heads.

Accordingly, an object of the invention is to provide new and improved means for and methods of holding dental dams. Here, an object is to provide dental dam frames which do not restrict the frontal area from which a dentist, or assistant, can work on a patient's teeth.

Still another object of the invention is to provide dental dams which are more comfortable for the patient.

Yet another object is to provide a complete sanitary dental dam support system which does not transfer germs, hair oils, or the like, from patient to patient.

A further object is to provide a frame which is free to rotate about the notch of the chin to a point of minimum stress from a stretched rubber sheet, thereby reducing stress upon the soft facial tissues to a minimum.

In keeping with an aspect of the invention, these and other objects are accomplished by a dental dam frame which at least partially surrounds a much greater arcuate portion of the patient's face, as compared to the portion surrounded by frames used heretofore. The frame includes a plurality of fasteners for attaching thereto an elastic dental dam. Other fasteners are integrally built on to the frame so that it may be tied in place about a patient's head, preferably by means of disposable dental tape. The geometry of the frame relative to the mouth is such that the dental dam does not restrict either the working or the visible area of the patient's mouth.

An embodiment of the invention may be understood best from the attached drawings, wherein:

FIG. 1 is a pictorial representation of a patient with a first embodiment of the inventive dental dam installed;

FIG. 2 is a perspective view of the prior art McConville frame for supporting a dental dam;

FIG. 3 schematically indicates how the prior art frame of FIG. 2 creates problems by restricting the working and visual area for both a dentist and a dental assistant;

FIG. 4 is a perspective view of a first embodiment of the inventive frame;

FIG. 5 schematically indicates how the invention provides an improved field of work and vision as compared to the prior art frame of FIGS. 2 and 3;

FIG. 6 illustrates an alternative method of anchoring dental tape used to hold the inventive frame in place;

FIG. 7 pictorially shows both the skull and facial tissues of a patient in order to illustrate the preferred location of the inventive dental dam frame with respect to recognized index points on a skull;

FIG. 8 is a plan view of the bottom of a second embodiment of the invention;

FIG. 9 is a front elevation view of the second embodiment;

FIG. 10 is a side elevation view of the second embodiment;

FIG. 11 is a plan view of a stake used to anchor the rubber dental dam;

FIG. 12 is a side elevation view of a tie anchor for the frame; and

FIG. 13 is a front elevation view of the same tie anchor.

The dental dam 20 (FIG. 1) is conventionally a thin sheet of rubber used for keeping a patient's teeth clean and dry while they are being cut, filled or otherwise repaired. By known techniques, small holes are first punched into the sheet of rubber at the relative location of each tooth (e.g., at 22) that is to project through and be exposed to view when the dam 20 is in place. To install the dam, the dentist places each hole over the corresponding tooth and then see-saws the rubber sheet back and forth over the corresponding teeth. This motion stretches the rubber of the dam so that it tightly surrounds each of the teeth, passing between them and then down to the gum line.

Next, any suitable known spring clamps 24,26 are expanded, slipped over appropriate teeth, and released. The spring contracts under its own internal spring tension and tightly grips the tooth, above the rubber sheet. This holds the rubber sheet and keeps it from being dislodged.

The rubber sheet is first installed over the patient's teeth, a rubber napkin is then placed between the sheet and the patient's face and the rubber sheet is attached to a generally U-shaped frame 28. The inventive frame 28 is large enough to span the entire chin area of the patient and to fit on opposite sides of the face. Next, for a right-handed operator, a section of dental tape 38 is attached to one corner 32 of the frame 28, passed behind the patient's head, drawn sufficiently tight and attached to an opposite corner 30 of the frame, in a similar manner. (Dental tape is a heavy ribbon-like version of conventional waxed dental floss which almost all dentists have on hand, as an office staple.) If a greater amount of contact area is required between the patient's head and the dental tape, it may be threaded through one or more layers of gauze strips to provide a pad at the back of the head.

An advantage of this method of dam installation is that the rubber sheet may be gently hooked onto the frame after a rubber dam napkin is placed between the rubber sheet and the face. As the rubber sheet is pulled taut, the pressure is equalized in all directions. Discomfort to the lower lip and face is greatly reduced due to the contoured support away from the tissues. There is a tendency for the rubber sheet to be better fitted to the individual variations in the contours of soft facial tissue, with less stretching of tissues because the sheet is hooked over the frame before the retraction is obtained.

The two upright members of the frame are equally spaced on opposite sides of the head and face, along vertical lines falling between the ears and the corners of the mouth, when the head is viewed in profile. The tension in the taut rubber sheet, pulling against the head bands 38,39, holds the frame 28 in a stable and secure position, which is a position of minimum tension in the rubber sheet. Therefore, the dentist may rest a finger against the frame for greater security and stability while working on a patient's teeth.

The nature of the improved frame will become more apparent from a comparison and contrast with the dam-holding devices that were used heretofore. The prior art method which incorporates frames similar to the frame 42 shown in FIGS. 2, 3, has a generally U-shaped form with a relatively narrow width W which merely covered the restricted portion of the mouth on which the dentist happens to be working. As seen in FIG. 3, the prior art frame 42 subtends an arc 48 which is restricted to about one-third of the total dental arch. Also, the nature of this prior art frame 42 is such that the rubber sheet is often first installed on the frame by hooking it over prongs such as 46 projecting outwardly from frame 42. Then, the dam (with the frame attached) must be worked on, over the teeth. When the dam is in its final position, the upright bars are pressed against and held by the soft cheek tissues. The dentist must be ever watchful to be sure that a part of the frame does not strike the patient's eye. The inventive frame has reduced this problem due to a shorter vertical dimension to the frame, as compared to the vertical dimension of prior devices. Of course, individual dentists may also elect to attach the sheet to the teeth first and, thereafter, to the frame.

After the dam has been fitted over the teeth (FIG. 3), frame 42 is rather loosely suspended in front of the teeth. Since the working area is restricted to the arc 48, the dentist may only insert and use his tools 50 on one side of the frame because the dental assistant also has to hold certain tools 52 in the oral cavity within the opposite side of the frame. Therefore, it is extremely awkward to work in the restricted area of the arc 48, especially when practicing "four-handed" dentistry (where the dentist operates with an assistant) and when doing "quadrant" dentistry (restoring all of one side or an arch, particularly the posterior teeth).

Also, the smaller area of contact between the frame 42 and the patient's face results in imbalanced forces upon the frame. The installation requirements are such that the frame is unstably mounted. Therefore, the dentist cannot rest his finger on the frame 42 with the same degree of stability that he can rest it upon the inventive frame.

The inventive dam holder (FIGS. 4, 5) corrects most of these problems and provides superior results, increased usefulness, economy, and ease of use. Sterilization procedures are easy and patients are more comfortable.

Briefly, according to the invention, the basic structure of the inventive frame (FIGS. 4, 5) entails a use of plastic (preferably nylon or fluorocarbon resins, such as duPont's TEFLON resin) in a facially contoured frame, with a generally U-shape configuration extending around the mandible and with uprights generally parallel to the facial plane of the face, which plane is defined by a line including the nasion to pogonion. The plastic material should be sufficiently heat-resistant so that it may be sterilized in an autoclave, and should be substantially rigid, have high strength, and be water-resistant. Since the frame is a one-piece unit, application is easy. A smooth retraction and large working field is created.

In greater detail, the inventive U-shaped frame 28 (FIGS. 4, 5) includes a pair of uprights 62,64 interconnected by a facial bow 66 (the bottom of the "U" shape) which is generally positioned in front of and may rest upon the chin. A predetermined number of stakes (such as 68) are formed on both of the uprights 62,64 and on the facial bow 66 of the frame. According to the invention, there are preferably four stakes on each upright and four more on the facial bow; however, another number of stakes may be provided. These stakes are positioned to project outwardly from the frame 28 in locations and at an angle which may be used to hook into and securely hold the rubber dam, without snagging the dentist, patient, or their clothing. Preferably, these stakes are integrally molded into the plastic of the frame itself. The stake points are not sharp enough to scratch a person, but they are sharp enough to easily grasp the rubber sheet when it is stretched over the stakes.

A vertically-oriented pair of generally T-shaped slots 70–76 and cleats 78–84 are oppositely disposed on the vertical members 62,64. Each of the T-shaped slots 70–76 includes a horizontal portion which enables a length of dental tape to pass therethrough. Each of the T-shaped slots 70–76 also includes a vertical portion which enables minor adjustments in the vertical positions of the dental tape to accommodate different patient requirements. This way, the relative dental tape frame positions may be adjusted according to head size and shape.

Each of the cleats 78–84 comprises a pair of horns, as shown at 82,84. Hence, the dental tape which is slipped into slot 70 (for example) may be looped around each of the horns, in turn. The last loop is inverted and pulled tightly to take a bite upon one of the horns. This way, the rubber dam frame 28 may be quickly and easily tied securely to the patient's head by means of disposable dental tape so that no structure is ever transferred from one to another patient's head, except for the frame which may be sterilized.

FIG. 5 is similar to FIG. 3 and shows that the dentist may work over a very wide arc 88, as compared to the relatively narrow work arc 48 of the prior art frame 48.

FIG. 6 shows an alternative embodiment for anchoring the end of the dental tape. Instead of using the cleat 78 shown in FIG. 4, the embodiment of FIG. 6 includes a slot 90 into which the dental tape 92 may be wedged after it is drawn through slot 70, to hold the tape 92 in position.

FIG. 7 shows the desired position of the inventive frame relative to well-known anatomical points on the patient's head. In greater detail, the facial plane includes the nasion 100 and the pogonion 102. The upright members 62,64 of the inventive frame should be substantially parallel to the facial plane and located approximately one-quarter of the distance extending from the ear 106 to the facial plane. In this position, the origin of the upright frame members is approximately over the gonion.

A second embodiment of the invention is seen in FIGS. 8–13. This embodiment is proportioned and shaped to fit a normal human face in the manner described above in connection with the first embodiment of FIGS. 1–7. Preferably, this frame is made of a white nylon, which is injection-molded.

Since all human heads have a remarkably uniform shape and size, the structural details of this embodiment of the inventive frame is best given by setting forth the physical measurements of the frame in one exemplary embodiment. More particularly, the bottom bar 120 (FIG. 8) of the frame is an arc of a circle having an inside radius of 2.80 inches. Five points or stakes 122,124,126,128,130 are formed on the bottom bar 120. Three of these stakes 122,124,128 project forwardly from the bar and two 120,130 project downwardly from the bar. Each of the stakes 124,128 is displaced from the center stake 122 by an angle B, which is 25° in this embodiment. Each of the stakes 126,130 on the bottom bar is displaced from the center stake 122 by an angle C, which is 50°. The thickness t of the bar is approximately a quarter inch.

From each of the outside ends of the base bar 120, two uprights 132,134 raise vertically to a height of 3.4 inches, in this embodiment. Since the bottom of the bar 120 has a thickness j which is essentially a third to a half inch, the inside dimension I of the uprights 132,134 is about three inches. Five stakes 140-148 are formed to project from the side of each upright, at the heights D-H which are, respectively: 0.7, 1.7, 2.2, 2.7 and 3.2 inches. The stake 140 points downwardly while the remainder point horizontally, to the side.

Each of the stakes 120,122 ... 148 is shaped, as shown in FIG. 11. They project outwardly for a distance which is something less than a quarter inch and they have a generally blunt end. When a rubber sheet is stretched over the point, its tension tends to grip the stake without damage to the sheet. The sheet is applied behind the frame, outside the uprights, and is then brought around and attached to the side stakes. The sheet goes under the bottom bar and up over the front stakes 122,124,128.

When the frame is applied to the face, the bottom bar 120 rests in and pivots about pogonion 102 (which is sometimes called the notch of the chin). Since the inside span S of the base bar 120 is about 5 inches, the uprights 132,134 do not encounter the soft facial tissues, but pass on opposite sides of the face and head, as the frame pivots about the point 102. Instead, it comes to rest in a position which is substantially parallel to the facial plane, when the dam is properly installed. It is not important whether the patient's facial plane is vertical or slightly off vertical since the position of the uprights, in effect, becomes self-adjusting to the patient's facial contours because they have an effect upon the tension in the dam.

The frame is tied around the patient's head by a dental tape which is looped around four anchor posts 150,152,154,156. Each of these anchor posts has a center post 160 terminated by a top flange 154. A slot 164 is formed in each of the flanges to receive and secure the end of the dental tape. These four anchor sets are preferably used to accommodate the economical injection molding.

In the foregoing description, physical dimensions were given to set forth the parameters of an exemplary frame for an adult. Naturally, a child's frame is slightly smaller. The various parameters are interrelated, and may be mutually varied somewhat. Thus, the measurements are given to illustrate the invention and not to be an exclusive limitation. Other dimensions may be selected from the adult dimensions given above. This is not to say, however, that normal human anatomy is so varied that any dimensions may be selected or that the frame dimensions will vary by gross amounts.

Those who are skilled in the art will readily perceive how to modify the system. Therefore, the appended claims are to be construed to cover all equivalent structures which fall within the true scope and spirit of the invention.

I claim:

1. A human facial frame for holding a dental dam, said frame having a generally U-shaped frame means comprising two upright members and an arcuate bottom member adapted to extend around and in front of a mandible, the arc of said bottom member having a radium which is less than 3 inches for surrounding a substantial arcuate portion of a patient's face and extending from molar to molar, said two upright members of the U-shaped frame means being adapted to be positioned on opposite sides of the face and head and in a position generally parallel to a facial plane which is defined by the nasion and the pogonion, said two upright members being adapted to be located in the range of approximately one-quarter of the distance extending from the ear to the facial plane, with the origin of the two upright frame members so located being adapted to rest over approximately the gonion on opposite sides of the patient's head when the bottom of the U-shaped means is positioned in and pivoted around the pogonion in the front of the chin, the frame including a plurality of outwardly projecting fastener means for securing a dental dam around the periphery of the U-shaped frame means, and other fasteners on the frame adapted to anchor dental tape tied in place about a patient's head.

2. The frame of claim 1 wherein said fastener means for securing the dental dam are a plurality of stakes spaced around the frame, there being more than eight of said fastener means.

3. The frame of claim 2 wherein there are fifteen of said stakes positioned on said frame to secure the rubber dam without snagging the patient or people working around the dam.

4. The frame of claim 1 or 2 and anchor posts on said frame adjacent each of said anchor posts terminating in an upper end flange with a radial slot formed in it.

5. The frame of claim 1 wherein the material from which it is constructed is a substantially rigid plastic material having heat and water-resistant properties and high strength, said plastic material being a type of material which tends to increase in its cure with each sterilization heat cycle.

6. A frame for a dental dam, said frame comprising a bottom bar having a generally arcuate configuration defining an inside span, said bottom bar terminating on opposite ends in upright posts, a plurality of fasteners distributed around said frame to secure a dental dam thereto, the inside span of said bar having a length which is great enough so that the bottom bar of said frame is adapted to rest on and pivot about the pogonion at the front of the chin of a patient with said upright posts passing on opposite sides of the patient's face without resting exclusively upon the soft facial tissue, said frame being adapted to rotate to and rest in a position wherein said uprights are approximately parallel to the facial plane.

7. The frame of claim 6 having dimensions such that, for an adult-sized frame, said arcuate bottom bar is an arc of a circle having a radius in the order of 2.8 inches and said span is in the order of 5 inches measured across said arc.

8. The frame of claim 7 wherein the uprights on an adult-sized frame raise to have approximately a three-inch inside dimension.

9. The frame of claims 7 or 8 wherein said frame is a child-sized frame with the noted proportions.

* * * * *